(12) United States Patent
Weber

(10) Patent No.: US 7,897,159 B2
(45) Date of Patent: Mar. 1, 2011

(54) PARAPOXVIRUSES IN COMBINATION WITH CLASSICAL CYTOTOXIC CHEMOTHERAPEUTIC AGENTS AS BIOCHEMOTHERAPY FOR THE TREATMENT OF CANCER

(75) Inventor: Olaf Weber, Wuelfrath (DE)

(73) Assignee: Aicuris GmbH & Co. KG, Wuppertal (DE)

( * ) Notice: Subject to any disclaimer, the term of this patent is extended or adjusted under 35 U.S.C. 154(b) by 229 days.

(21) Appl. No.: 12/123,360

(22) Filed: May 19, 2008

(65) Prior Publication Data

US 2009/0035269 A1 Feb. 5, 2009

Related U.S. Application Data

(63) Continuation of application No. PCT/EP2006/009855, filed on Oct. 12, 2006.

(30) Foreign Application Priority Data

Nov. 24, 2005 (EP) .................................. 05025600

(51) Int. Cl.
*A61K 39/275* (2006.01)

(52) U.S. Cl. ................. 424/281.1; 424/232.1; 424/93.2

(58) Field of Classification Search ........................ None
See application file for complete search history.

(56) References Cited

U.S. PATENT DOCUMENTS

| 2003/0021769 A1* | 1/2003 | Weber et al. ............. 424/93.21 |
| 2006/0008471 A1 | 1/2006 | Weber et al. |

FOREIGN PATENT DOCUMENTS

| WO | WO-00/69455 | 11/2000 |
| WO | WO-02/04002 | 1/2002 |
| WO | WO-03/006654 | 1/2003 |

OTHER PUBLICATIONS

Glimelius et al (Acta Oncologica. 40:135-154, 2001).*
Cozzi et al., Curr. Med. Chem.—Anti-Cancer Agents (2004) 4:93-121.
Friebe et al., Journal of Virology (2004) 78(17):9400-9411.
International Preliminary Report on Patentability for PCT/EP2006/009855, dated Feb. 28, 2008, 7 pages.
International Search Report for PCT/EP2006/009855, mailed on Feb. 9, 2007, 3 pages.
Kirn et al., Nature Medicine (2001) 7(7):781-787.
Martuza et al., Science (1991) 252:854-856.
Smith et al., Journal of Clinical Oncology (1996) 14:287-295.
Southam, NY Academy of Sciences (1960) 22:657-673.
Written Opinion for PCT/EP2006/009855, dated Feb. 28, 2008, 6 pages.

* cited by examiner

*Primary Examiner*—Mary E Mosher
(74) *Attorney, Agent, or Firm*—Morrison & Foerster LLP

(57) ABSTRACT

The invention relates to a method for the production of a pharmaceutical composition for treating cancer by combining *Parapoxvirus ovis* with at least one anticancer agent. The invention furthermore relates to a method for treating a patient afflicted with cancer comprising the administration of *Parapoxvirus ovis* in combination with at least one anticancer agent.

12 Claims, 1 Drawing Sheet

PARAPOXVIRUSES IN COMBINATION WITH CLASSICAL CYTOTOXIC CHEMOTHERAPEUTIC AGENTS AS BIOCHEMOTHERAPY FOR THE TREATMENT OF CANCER

CROSS-REFERENCES TO RELATED APPLICATIONS

This application is a continuation of co-pending international patent application PCT/EP2006/009855 filed on Oct. 12, 2006 and designating the U.S., and claims priority of European patent application EP 05 025 600.7 filed on Nov. 24, 2005. The contents of the above-referenced applications are incorporated herein by this reference in their entirety.

BACKGROUND OF THE INVENTION

1. Field of the Invention

The invention relates to the production of a pharmaceutical composition for treating cancer, and to a method for treating a patient afflicted with cancer.

2. Related Prior Art

In the search for novel cancer therapies that can be used in conjunction with existing treatments, the use of virus-based therapies holds some promise (1). Viruses have evolved to infect cells and often destroy these cells through diverse mechanisms. Although a number of viruses have been used in the clinic so far, this approach has suffered from toxicity, infection of unrelated tissues, immunological side effects and, therefore, was abandoned (2). However, recombinant DNA technology offered new possibilities to use viruses in therapeutic approaches. Current attempts use replication-selective viruses (reviewed in 1). Such viruses should replicate selectively in dividing cells (3). However, although these viruses may rapidly spread in cell-culture monolayers, spread within solid tumors remains an unsolved problem (1).

The use of inactivated *Parapoxvirus ovis* for cancer therapies has been suggested previously (4).

Interferon-α (IFN-α) has previously been investigated with classical chemotherapeutics, i.e., cisplatin, vinclesine and dacarbacine. The combination of biologicals and cytotoxic chemotherapeutics is called biochemotherapy. After biochemotherapy, responder rates are up to 66% and, therefore, superior compared to cytotoxic chemotherapy (5).

The use of inactivated viruses for biochemotherapy in cancer therapies has not been reported.

As is clear from the abovementioned prior art, no therapeutic method has so far been disclosed which uses an inactivated virus as an immunomodulating agent and a classical cytotoxic chemotherapeutic agent as a biochemotherapy for cancer.

SUMMARY OF THE INVENTION

The present invention is therefore based on the technical problem of providing a therapeutic method which not only reduces the tumor burden of patients more effectively compared to cytotoxic chemotherapy but also provides a therapeutic method for the reconstitution of the immune system after cytotoxic chemotherapy. This therapeutic method should not only have fewer or no undesirable side effects, it also should be superior to current therapies.

The present invention relates to:

1. The use of *Parapoxvirus ovis* in combination with at least one additional anticancer agent for the preparation of a medicament for treating cancer. The invention furthermore relates to the use of *Parapoxvirus ovis* for the production of a medicament for treating cancer in combination with at least one additional anticancer agent. Another aspect of the invention relates to the use of *Parapoxvirus ovis* for treating a patient afflicted with cancer, wherein at least one additional anticancer agent is given to said patient to treat cancer. Furthermore, the invention relates to methods of treatment of cancer, in which *Parapoxvirus ovis* is administered in combination with other anticancer agents.

According to the invention *Parapoxvirus ovis* is understood to be *Parapoxvirus ovis* strain D1701, NZ-2, NZ-7, NZ-10 or orf-11.

The invention also relates to the use of derivatives of the abovementioned *Parapoxvirus ovis* obtained by passaging or adaptation using suitable cell systems such as for example human cells such as WI-38, MRC-5, monkey cells, e.g., Vero cells, bovine cells, such as for example BL-K13A47/Reg or MDBK, and ovine cells such as MDOK, in combination with substances which are effective in anticancer therapy for the production of medicaments against cancer in humans and animals.

In addition, the invention relates to the use of parts or fragments of the abovementioned *Parapoxvirus ovis* and their passaging and adaption variants in combination with substances which are effective in anticancer therapy. According to the invention, parts or fragments of a virus are understood to be genomic or subgenomic fragments of the whole virus or of its genomic nucleic acid, or other components of the virus, which are expressed by means of suitable vectors such as vaccinia viruses in suitable systems such as fibroblast cell cultures. In a preferred variant the parts or fragments of the *Parapoxvirus ovis* according to the invention are purified by conventional methods, such as for example by filtration or chromatography. In another preferred variant the parts or fragments of the *Parapoxvirus ovis* according to the invention are produced by recombination by methods known to the skilled man. According to the invention, cancer is all human and animal diseases associated with proliferating or resting tumors.

In a preferred variant of the invention the anticancer agent is a cytotoxic agent.

2. The present invention also relates to a use according to item 1, wherein the cancer is melanoma, breast cancer, prostate cancer, lung cancer, colorectal cancer, liver cancer or metastatic disease of one or more of the primary cancer.

3. The present invention also relates to the use according item 1 or 2, wherein the *Parapoxvirus ovis* is *Parapoxvirus ovis* strain D1701, NZ-2, NZ-7, NZ-10 or orf-11. In a further variant of the invention the *Parapoxvirus ovis* is a *Parapoxvirus* obtained by passaging of these strains.

4. The present invention also relates to the use according to one of the items 1 to 3, wherein the *Parapoxvirus ovis* is present in an inactivated form. The inactivation of the *Parapoxvirus* is carried out by virus inactivation methods known to the skilled man. In a preferred variant the *Parapoxvirus ovis* is inactivated by the method described in European Patent No. EP-B1-0312839.

5. The present invention also relates to the use according to one of the items 1 to 4, wherein the treatment of cancer produces a reduction of tumor size of patients, i.e., the medicament causes a reduction of the tumor size or mass, respectively.

6. The present invention also relates to the use according to one of the items 1 to 5, wherein the treatment of cancer reduces the number and size of metastases of the primary tumors as measured by procedures known to the skilled man.

7. The present invention also relates to the use according to one of the abovementioned items 1 to 6, wherein the anticancer agent is selected from the group consisting of asparaginase, bleomycin, carboplatin, carmustine, chlorambucil, cisplatin, colaspase, cyclophosphamide, cytarabine, dacarbazine, dactinomycin, daunorubicin, doxorubicin (adriamycin), epirubicin, etoposide, 5-fluorouracil, hexamethylmelamine, hydroxyurea, ifosfamide, irinotecan, leucovorin, lomustine, mechlorethamine, 6-mercaptopurine, mesna, methothrexate, mitomycinC, mitoxantrone, prednisolone, prednisone, precarbazine, raloxifen, streptozocin, tamoxifen, thioguanine, topotecan, vinblastine, vincristine, vindesine, amnogluthethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentstatin, PALA, plicamycin, semustine, teniposide, testosterone propionate, thiotepa, trimethylmelamine, uridine, and vinorelbine, oxaliplatin, gemcitabine, capecitabine, epothilone and its natural or synthetic derivatives, tositumomab, trabedectin, and temozolomide, trastuzumab, cetuximab, bevacizumab, pertuzumab, ZD-1839 (Iressa), OSI-774 (Tarceva), CI-1033, GW-2016, CP-724,714, HKI-272, EKB-569, STI-571 (Gleevec), PTK-787, SU-11248, ZD-6474, AG-13736, KRN-951, CP-547, 632, CP-673,451 and sorafenib.

The pharmaceutical composition of the present invention may be administered in oral forms, such as, without limitation, normal and enteric coated tablets, capsules, pills, powders, granules, elixirs, tinctures, solution, suspensions, syrups, solid and liquid aerosols and emulsions. They may also be administered in parental forms, such as, without limitation, intravenous, intraperitoneal, subcutaneous, intramuscular, intratumoral and the like forms well-known to those of ordinary skill in the pharmaceutical arts. The pharmaceutical composition of the present invention can be administered in intranasal form via topical use of suitable intranasal vehicles, or via transdermal routes, using transdermal delivery systems well-known to those of ordinary skilled in the art.

The dosage regimen with the use of the pharmaceutical composition of the present invention is selected by one of ordinary skill in the arts, in view of a variety of factors, including, without limitation, age, weight, sex, and medical condition of the recipient, the severity of the condition to be treated, the route of administration, the level of metabolic and excretory function of the recipient, the dosage form employed.

The pharmaceutical compositions of the present invention are preferably formulated prior to administration and include one or more pharmaceutically acceptable excipients. Excipients are inert substances such as, without limitations, carriers, diluents, flavoring agents, sweeteners, lubricants, solubilizers, suspending agents, binders, tablet disintegrating agents and encapsulating material.

The formulation may be in unit dosage form, which is a physically discrete unit containing a unit dose, suitable for administration in human or other mammals. A unit dosage form can be a capsule or tablets, or a number of capsules or tablets. A "unit dose" is a predetermined quantity of the active pharmaceutical composition of the present invention, calculated to produce the desired therapeutic effect, in association with one or more excipients. Dosages will vary from about $10^3$ to about $10^{12}$ physical number of viral particles per application or will be based an physical number of particles/kg/day.

The pharmaceutical compositions of the present invention may be administered in a single daily dose, or the total daily dose may be administered in divided doses, two, three, or more times per day. Where delivery is via transdermal forms, of course, administration is preferably continuous.

DESCRIPTION OF PREFERRED EMBODIMENTS

Figure 1:
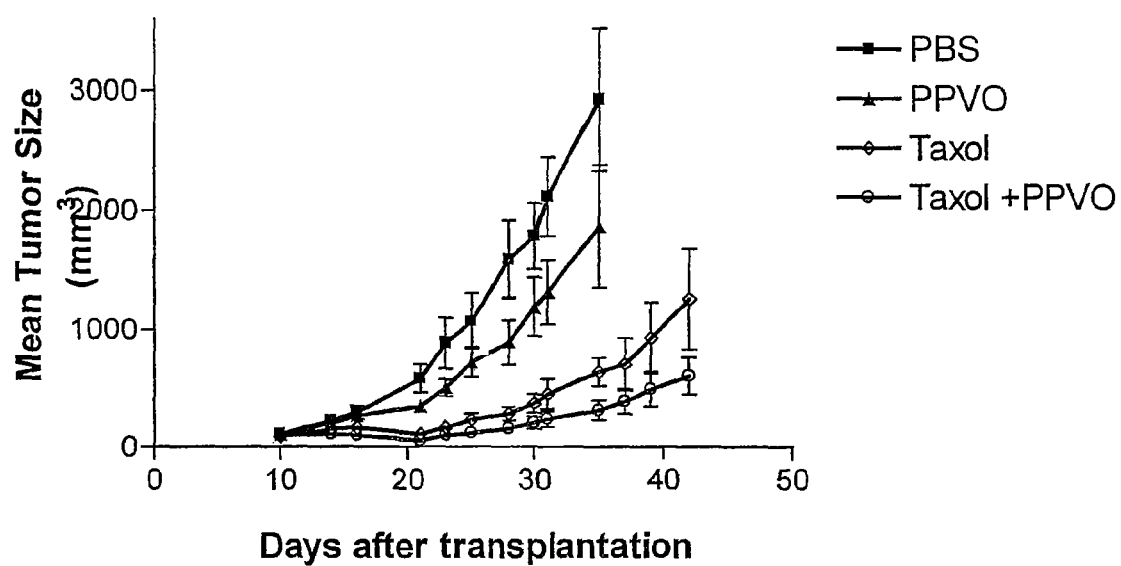
FIG. 1 shows that the anti-tumor activity of a *Parapoxvirus ovis* (PPVO) and Taxol combination is superior to a monotherapy with either taxol or PPVO in an MDAMB 231 breast cancer model in nude mice. Paclitaxel (Taxol®, Bristol Myers Squibb) was administered at 7.5 mg/kg/day i.v. on three consecutive days starting day 10. A single dose of PPVO ($1 \times 10^6$ TCID$_{50}$) or the respective placebo was administered day 13 after transplantation intraperitoneally (n=10 mice/group).

MDA-MB-231 human breast carcinoma cells (ATCC # HTB26) were cultured in standard universal growth medium (UM: DMEM, 10% FBS, 10 mM HEPES, 2 mM L-glutamine, 100 U/ml penicillin, 100 μg/ml streptomycin) at 37° C. in 5% CO$_2$ in a humidified incubator. The cells were harvested by trypsinization, washed, counted, adjusted to $2.5 \times 10^7$ cells/ml with ice cold phosphate-buffered saline (PBS), and subsequently stored on ice until transplantation. Approximately $5 \times 10^6$ cells in a total volume of 0.2 ml PBS are injected subcutaneously (s.c.) in the flank region. Eight-to-ten week-old female NCr nude mice (Taconic, Germantown, N.Y.) with an average body mass of about 20-25 g were used for the experiments. Tumor measurements were performed 10 days after transplantation. Tumor sizes were calculated using the formula (a×b×b)/2. Thereafter the mice were randomized and divided into several groups that reflect different treatments (n=10 mice/group). In the first group the mice only received PBS as a control approach. In the second group Paclitaxel (Taxol®, Bristol Myers Squibb) was administered at 7.5 mg/kg/day i.v. on three consecutive days starting day 10. In the third group a single dose of PPVO ($1 \times 10^6$ TCID$_{50}$) was administered day 13 after transplantation intraperitoneally. In the fourth group the administration of Paclitaxel and PPVO according to the dosage regimen applied to groups two and three was combined. For reasons of animal welfare, animals were sacrificed when the tumors reached approximately 10-15% of the mouse body weight or when the tumors scabbed or ulcerated.

As it can be seen in FIG. 1 the mean tumor size is clearly reduced in group four (−●−) if compared to group two (−◆−) or group three (−▲−).

Therefore, the inventors clearly demonstrated for the first time that the administration of a combination of *Parapoxvirus ovis* (PPVO) and a conventional anticancer agent is superior to a monotherapy with either the anticancer agent or PPVO alone.

REFERENCES

1. D. Kirn, R. J. Martuza, J. Zwiebel, *Nat. Med.* 7, 781 (2001)
2. C. M. Southam, *NY Acad. Sci.* 22, 656 (1960)
3. R. L. Martuza, A. Malick, J. M. Markert, K. L. Ruffner, D. M. Coen, *Science* 252, 856 (1991)

4. O. Weber et al. WO 02/04002
5. S. S. Legha *J. Clin. Oncol.* 14, 7 (1996) FSHβ

The invention claimed is:

1. A method for the production of a pharmaceutical composition for treating cancer, comprising the provision of *Parapoxvirus ovis* and at least one anti-cancer agent, and the formulation of said *Parapoxvirus ovis* in combination with said at least one anti-cancer agent into a pharmaceutical acceptable carrier, wherein said anti-cancer agent is a cytotoxic agent.

2. The method according to claim 1, wherein said cancer is selected from the group consisting of: melanoma, breast cancer, prostate cancer, lung cancer, colorectal cancer, liver cancer, bladder cancer, cancer of the endocrine system, cancer of the nervous system, lymphoma and metastatic disease of the respective primary cancer.

3. The method according to claim 1, wherein said *Parapoxvirus ovis* is selected from the group consisting of: *Parapoxvirus ovis* strains D1701, NZ-2, NZ-7, NZ-10, orf-11, and a *Parapoxvirus ovis* strain obtained by any passaging of before identified strains.

4. The method according to claim 1, wherein said *Parapoxvirus ovis* is present in an inactivated form.

5. The method according to claim 1, wherein said pharmaceutical composition causes a reduction of tumor size or tumor mass.

6. The method according to claim 1, wherein said anti-cancer agent is selected from the group consisting of: vinblastine, vincristine, docetaxel, and paclitaxel.

7. A method for treating a patient afflicted with cancer, comprising the step of the administration of *Parapoxvirus ovis* in combination with at least one anti-cancer agent, wherein said anti-cancer agent is a cytotoxic agent.

8. The method of claim 7, wherein said cancer is selected from the group consisting of: melanoma, breast cancer, prostate cancer, lung cancer, colorectal cancer, liver cancer, bladder cancer, cancer of the endocrine system, cancer of the nervous system, lymphoma, and metastatic disease of the respective primary cancer.

9. The method of claim 7, wherein said *Parapoxvirus ovis* is selected from the group consisting of: *Parapoxvirus ovis* strains D1701, NZ-2, NZ-7, NZ-10, orf-11, and a *Parapoxvirus ovis* strain obtained by any passaging of before identified strains.

10. The method of claim 7, wherein said *Parapoxvirus ovis* is present in an inactivated form.

11. The method of claim 7, wherein said administration causes a reduction of tumor size or tumor mass.

12. The method of claim 7, wherein said anti-cancer agent is selected from the group consisting of: vinblastine, vincristine, and paclitaxel.

* * * * *